United States Patent
Moses et al.

(10) Patent No.: US 7,858,324 B2
(45) Date of Patent: Dec. 28, 2010

(54) CYR61 AS A BIOMARKER FOR DIAGNOSIS AND PROGNOSIS OF CANCERS OF EPITHELIAL ORIGIN

(75) Inventors: Marsha A. Moses, Brookline, MA (US); Bo Zhang, Arlington, MA (US)

(73) Assignee: Children's Medical Center Corporation, Boston, MA (US)

( * ) Notice: Subject to any disclaimer, the term of this patent is extended or adjusted under 35 U.S.C. 154(b) by 167 days.

(21) Appl. No.: 11/815,831

(22) PCT Filed: Feb. 17, 2006

(86) PCT No.: PCT/US2006/005812

§ 371 (c)(1), (2), (4) Date: Mar. 24, 2008

(87) PCT Pub. No.: WO2006/089212

PCT Pub. Date: Aug. 24, 2006

(65) Prior Publication Data

US 2008/0286811 A1    Nov. 20, 2008

Related U.S. Application Data

(60) Provisional application No. 60/654,111, filed on Feb. 18, 2005.

(51) Int. Cl.
*G01N 33/53* (2006.01)
(52) U.S. Cl. .............................. 435/7.1; 435/6; 530/350
(58) Field of Classification Search .................. 435/7.1, 435/6; 530/350
See application file for complete search history.

(56) References Cited

U.S. PATENT DOCUMENTS

2004/0086504 A1 *   5/2004   Sampath et al. .......... 424/143.1

FOREIGN PATENT DOCUMENTS

WO    WO 01/98359 A    12/2001
WO    WO 03/024308 A2   3/2003

OTHER PUBLICATIONS

Ohkaru et al, 1995, J Immunol method, 178: 99-111.*
Muramatsu Y. et al. "Early detection of cysteine rich protein 61 (CYR61, CCN1) in urine following renal ischemic reperfusion injury" Kidney International, New York, NY, US, vol. 62, No. 5, Nov. 1, 2002, pp. 1601-1610, XP002966736 ISSN: 0085-2538.
Pilarsky C.P. et al. "Expression of the Extracellular Matrix Signaling Molecule CYR61 Is Downregulated in Prostate Cancer" Prostate, Wiley-Liss, New York, NY, US, vol. 36, Jan. 1, 1998, pp. 85-91, XP002908329 Issn: 0270-4137.
Kunz M. et al. "Mechanisms of hypoxic gene regulation of angiogenesis factor Cyr61 in melanoma cells" Journal of Biological Chemistry, AL, vol. 278, No. 46, Nov. 14, 2003, pp. 45651-45660, xp003017167 ISSN: 0021-9258.
Mo et al. CYR61 (CCN1) is essential for placental development and vascular integrity. Mol. Cell Biol. Dec. 2002, vol. 22, No. 24, pp. 8709-8720 see abstract.
Sugita et al., Combined use of oligonucleotide and tissue microarrays identifies cancer/testis antigens as biomarkers in lung carcinoma. Cancer Res. Jul. 15, 2002;62(14):3971-9.

* cited by examiner

*Primary Examiner*—Misook Yu
*Assistant Examiner*—Minh Tam Davis

(57)    ABSTRACT

Urinary Cyr61 protein levels are up regulated in patients that have cancers of epithelial origin, i.e. breast cancer and ovarian cancer. Accordingly, the present invention is directed to methods for prognostic evaluation, and diagnosis of cancers of epithelial origin. Further, the amount of Cyr61 protein detected in a urine sample correlates with disease status such that Cyr61 levels can be used to predict the presence of, as well as the metastatic potential of cancer. Thus, measuring the level of Cyr61 in urine provides a quick, easy, and safe screen that can be used to both diagnose and prognose cancer in a patient.

16 Claims, 3 Drawing Sheets

```
  1 mssriarala lvvtllhltr lalstcpaac hcpleapkca pgvglvrdgc gcckvcakql
 61 nedcsktqpc dhtkglecnf gasstalkgi cragsegrpc eynsriyqng esfqpnckhq
121 ctcidgavgc iplcpqelsl pnlgcpnprl vkvtgqccee wvcdedsikd pmedqdgllg
181 kelgfdasev eltrnnelia vgkgsslkrl pvfgmepril ynplqggkci vqttswsqcs
241 ktcgtgistr vtndnpecrl vketricevr pcgqpvyssl kkgkkcsktk kspepvrfty
301 agclsvkkyr pkycgscvdg rcctpqltrt vkmrfrcedg etfsknvmmi qsckcnyncp
361 haneaafpfy rlfndihkfr d (SEQ ID NO:1)
```

FIG. 2

SEQUENCE LISTING

<160> NUMBER OF SEQ ID NOS: 1

<210> SEQ ID NO 1
<211> LENGTH: 381
<212> TYPE: PRT
<213> ORGANISM: Homo sapiens

<400> SEQUENCE: 1

```
Met Ser Ser Arg Ile Ala Arg Ala Leu Ala Leu Val Val Thr Leu Leu
 1               5                  10                  15

His Leu Thr Arg Leu Ala Leu Ser Thr Cys Pro Ala Ala Cys His Cys
            20                  25                  30

Pro Leu Glu Ala Pro Lys Cys Ala Pro Gly Val Gly Leu Val Arg Asp
        35                  40                  45

Gly Cys Gly Cys Cys Lys Val Cys Ala Lys Gln Leu Asn Glu Asp Cys
    50                  55                  60

Ser Lys Thr Gln Pro Cys Asp His Thr Lys Gly Leu Glu Cys Asn Phe
65                  70                  75                  80

Gly Ala Ser Ser Thr Ala Leu Lys Gly Ile Cys Arg Ala Gln Ser Glu
                85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Asp Gly Ala Val
        115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Thr Gly Gln Cys Cys Glu Glu
145                 150                 155                 160

Trp Val Cys Asp Glu Asp Ser Ile Lys Asp Pro Met Glu Asp Gln Asp
                165                 170                 175

Gly Leu Leu Gly Lys Glu Leu Gly Phe Asp Ala Ser Glu Val Glu Leu
            180                 185                 190

Thr Arg Asn Asn Glu Leu Ile Ala Val Gly Lys Gly Ser Ser Leu Lys
        195                 200                 205

Arg Leu Pro Val Phe Gly Met Glu Pro Arg Ile Leu Tyr Asn Pro Leu
    210                 215                 220

Gln Gly Gln Lys Cys Ile Val Gln Thr Thr Ser Trp Ser Gln Cys Ser
225                 230                 235                 240

Lys Thr Cys Gly Thr Gly Ile Ser Thr Arg Val Thr Asn Asp Asn Pro
                245                 250                 255

Glu Cys Arg Leu Val Lys Glu Thr Arg Ile Cys Glu Val Arg Pro Cys
            260                 265                 270

Gly Gln Pro Val Tyr Ser Ser Leu Lys Lys Gly Lys Lys Cys Ser Lys
        275                 280                 285

Thr Lys Lys Ser Pro Glu Pro Val Arg Phe Thr Tyr Ala Gly Cys Leu
    290                 295                 300

Ser Val Lys Lys Tyr Arg Pro Lys Tyr Cys Gly Ser Cys Val Asp Gly
305                 310                 315                 320

Arg Cys Cys Thr Pro Gln Leu Thr Arg Thr Val Lys Met Arg Phe Arg
                325                 330                 335

Cys Glu Asp Gly Glu Thr Phe Ser Lys Asn Val Met Met Ile Gln Ser
            340                 345                 350
```

```
-continued

Cys Lys Cys Asn Tyr Asn Cys Pro His Ala Asn Glu Ala Ala Phe Pro
        355                 360                 365
Phe Tyr Arg Leu Phe Asn Asp Ile His Lys Phe Arg Asp
    370                 375                 380
```

CYR61 AS A BIOMARKER FOR DIAGNOSIS AND PROGNOSIS OF CANCERS OF EPITHELIAL ORIGIN

CROSS-REFERENCE TO RELATED APPLICATIONS

This application is the national stage of International (PCT) Patent Application Serial No. PCT/US2006/005812, filed Feb. 17, 2006, and published under PCT Article 21(2) in English, which claims priority to and the benefit under 35 U.S.C. §119(e) of U.S. provisional Patent Application No. 60/654,111 filed Feb. 18, 2005; the contents of each application are incorporated herein by reference in their entirety.

FIELD OF THE INVENTION

The present invention relates to methods for the diagnosis and prognosis of cancers of epithelial origin by assessing levels of Cyr61 in a urine sample obtained form a patient.

BACKGROUND OF THE INVENTION

One of the most important factors in the survival of cancer is detection at an early stage. Clinical assays that detect the early events of cancer offer an opportunity to intervene and prevent cancer progression. With the development of gene profiling and proteomics there has been significant progress in the identification of molecular markers or "biomarkers" that can be used to diagnose and prognose specific cancers. For example, in the case of prostate cancer, the antigen PSA (for prostate specific antigen) can be detected in the blood and is indicative of the presence of prostate cancer. Thus, the blood of men at risk for prostate cancer can be quickly, easily, and safely screened for elevated PSA levels.

Even though there has been significant progress in the field of cancer detection, there still remains a need in the art for the identification of new biomarkers for a variety of cancers that can be easily used in clinical applications. For example, to date there are relatively few options available for the diagnosis of breast cancer using easily detectable biomarkers. Overexpression of EGFR, particularly coupled with down-regulation of the estrogen receptor, is a marker of poor prognosis in breast cancer patients. In addition, up-regulation of Cyr61 in breast cancer tumor tissue samples has been noted in U.S. patent application No. 20040086504, however, detection of Cyr61 involves invasive procedures and the use of urine for analysis of Cyr61 is not taught. Other markers of breast cancer include high levels of M2 pyruvate kinase (M2 PK) in blood (U.S. Pat. No. 6,358,683), high ZNF217 protein levels in blood (WO 98/02539), and differential expression of a newly identified protein in breast cancer, PDEBC, which is useful for diagnosis (U.S. patent application No. 20030124543). These biomarkers offer an alternative method of diagnosis, however, they are not widely used and many involve invasive procedures for detection. Furthermore, despite the use of a number of histochemical, genetic, and immunological markers, clinicians still have a difficult time predicting which tumors will metastasize to other organs.

The identification of biomarkers is particularly relevant to improving diagnosis, prognosis, and treatment of the disease. As such, there is need in the art to identify alternative biomarkers that can be quickly, easily, and safely detected. Such biomarkers may be used to diagnose, to stage, or to monitor the progression or treatment of a subject with cancer. Biomarkers can also be used to differentiate between organ confined and metastatic cancers.

Biomarkers that are involved in the "angiogenic switch" of tumors are particularly useful because tumor growth and metastasis are angiogenic dependent. When a tumor becomes angiogenic, the tumor expands progressively and can disseminate metastatic cells (Hanahan D, Folkman J., Cell 86:353-364, 1996; Smith-Mcune and Weidner N., Cancer Research, 54: 800-804). Thus, identification of biomarkers involved in the switch of a tumor to an angiogenic state will enable one to diagnose organ confined and metastatic cancer.

SUMMARY OF THE INVENTION

The present invention is based on the discovery that Cyr61 protein is present in urine of patients that have ovarian cancer and breast cancer and that the levels of Cyr61 protein are higher in patients that have malignant forms of such cancers. Accordingly, the present invention is directed to methods for prognostic evaluation, and to methods for facilitating diagnosis of cancers of epithelial origin such as breast cancer, colon cancer, prostate cancer, liver cancer, bladder cancer, pancreatic cancer, ovarian cancer, cervical cancer, lung cancer, and skin cancer, as well as others. Cyr61 as a marker for therapeutic efficacy is also disclosed.

In particular, monitoring levels of Cyr61 protein in urine can be used as a primary screen to facilitate the diagnosis of ovarian or breast cancer; a higher amount of Cyr61 protein detected in urine of a sample from a test patient as compared to an age and sex matched healthy control sample is indicative that the patient has cancer. In other words, there is an increased likelihood that the patient has cancer. Further tests to confirm diagnosis can then be performed, such as mammography (breast cancer), ultrasound, PET scanning, MRI or any other imaging techniques, biopsy, clinical examination, or ductogram. Furthermore, monitoring the levels of Cyr61 protein in a patient over time, and finding an increase in expression over time, can be used to indicate that the cancer has increased its aggressiveness, and thus the patient has a poor prognosis. The clinician can then adjust treatment. Thus, measuring the level of Cyr61 in urine provides a quick, easy, and safe screen that can be used to both diagnose and prognose cancer of epithelial origin, e.g., breast or ovarian cancer, in a patient.

Without being bound by theory, it is believed that Cyr61 is involved with the angiogenic switch. Therefore, detection of Cyr61 is believed to indicate that the cancer has switched to a more angiogenic disease and thus requires more aggressive treatment. In support of this, Cyr61 has been found to upregulate molecules involved in Epithelial Mesenchymal Transition (EMT) (See Example 3). EMT is an important process by which epithelial cells acquire mesenchymal, fibroblast-like properties and show reduced intercellular adhesion and increased motility. It is believed that EMT-like events occur during tumor progression and malignant transformation, endowing cancer cells with invasive and metastatic properties (Lionel Laruel and Alfonso Bellacosa Oncogene (2005) 24, 7443-7454).

In one embodiment, a method for facilitating the diagnosis of cancer of epithelial origin in a subject is provided. The method comprises measuring the level of Cyr61 present in a test urine sample obtained from a subject and comparing the observed level of Cyr61 with the level of Cyr61 present in a control urine sample. Higher levels of Cyr61 in the test sample, as compared to the control sample, is indicative of an increased likelihood of cancer. Preferably, the level is 1.5-fold, more preferably 2-fold or greater, more than that of the control.

Preferably the methods of the invention are used for early detection of cancers of epithelial origin, especially breast and ovarian cancer. For example, a subject can be screened by a physician during their annual physicals. A positive test result, wherein the levels of Cyr61 are higher than that of the control would warrant further diagnostic evaluation.

The term "control sample" refers to a urine sample obtained from a "normal" or "healthy" individual(s) that is believed not to have cancer. Controls may be selected using methods that are well known in the art. Once a level has become well established for a control population, array results from test urine samples can be directly compared with the known levels.

The term "test sample" refers to a urine sample obtained from a patient being tested for a cancer of epithelial origin.

In one aspect, the cancer of epithelial origin to be diagnosed is breast cancer, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovarian cancer, cervical cancer, lung cancer, and skin cancer, such as squamous cell and basal cell cancers, prostate cancer, renal cell carcinoma, and other known cancers that effect epithelial cells throughout the body. Preferably the cancer is breast cancer or ovarian cancer.

The present invention also contemplates the assessment of the level of Cyr61 present in multiple test samples obtained from the same subject, where a progressive increase in the amount of Cyr61 over time indicates an increased aggressiveness (e.g. metastatic potential) of the cancer tumor. As such, the levels of Cyr61 serve as a predictor of disease status and stage. Samples can be taken, days, weeks, or months apart from one another.

The present invention further contemplates the assessment of Cyr61 levels to monitor the therapeutic efficacy of a treatment regime designed to treat a patient having a cancer of epithelial origin.

In one aspect of the invention, Cyr61 levels present in a test urine sample are measured by contacting the test sample, or preparation thereof, with an antibody-based binding moiety that specifically binds to Cyr61 protein, or to a portion thereof. The antibody-based binding moiety forms a complex with Cyr61 that can be detected, thereby allowing the levels of Cyr61 to be measured.

Antibody-based immunoassays are the preferred means for measuring levels of Cyr61 protein. However, any means known to those skilled in art can be used to assess Cyr61 levels. For example, in some embodiments Cyr61 expression levels are assayed by mass spectrometry, including SELDI mass spectrometry.

In a further embodiment, the invention provides for kits that comprise means for measuring Cyr61 in a urine sample.

In another embodiment, a method to direct treatment of a subject is provided. The method comprises having a subject tested for the levels of Cyr61 in a urine sample obtained from the subject, wherein a clinician reviews the results and if the urine has a higher level of Cyr61 than the level of Cyr61 in the control sample, the clinician directs the subject to be treated for cancer of epithelial origin. The test may be performed in the same country where the subject resides or in another country and the results are made available, for example via a Web site, or are transmitted to the clinician.

Other aspects of the invention are disclosed infra.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIG. 1a; an immunoblot detecting Cyr61 immunoreactive protein in urine from ovarian cancer patients (OV3, OVCAR3 cell extracts; Control, control sample; Benign, urine from a patient with benign cancer; Malignant, urine from a patient with malignant cancer. FIG. 1b; a bar graph quantitation of immunoblots detecting Cyr61 immunoreactive protein in urine from ovarian cancer patients. n=12 for each stage.

FIG. 2 shows the amino acid sequence for Cyr61 (SEQ ID NO:1).

DETAILED DESCRIPTION OF THE INVENTION

Figure 1A:
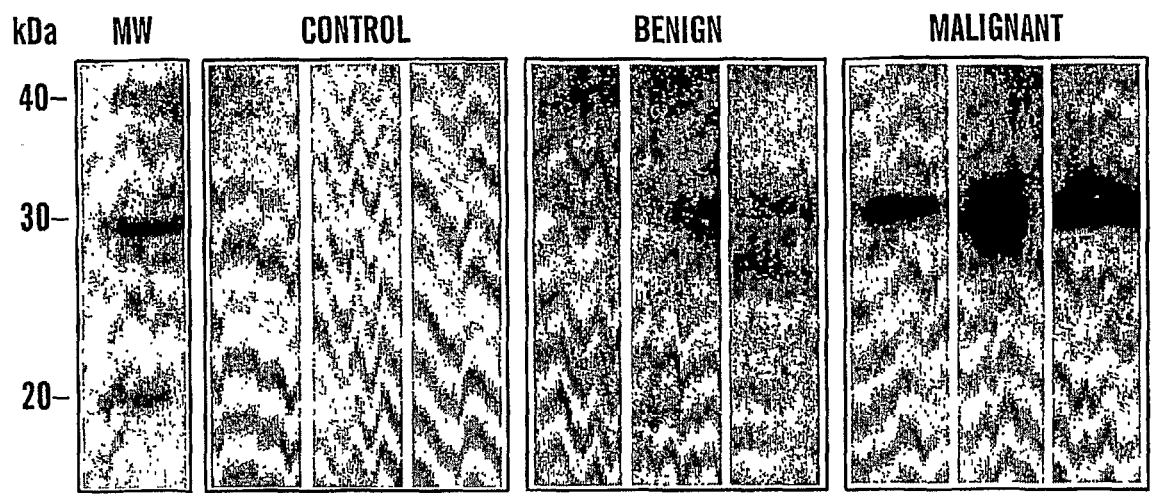
FIGS. 1a and 1b show that Cyr61 is detected in the urine of ovarian cancer patients.

We have discovered that the levels of Cyr61 present in urine samples of patients correlate with the presence, or absence of, cancers of epithelial origin.

As used herein, "cancers of epithelial origin" refers to cancers that arise from epithelial cells which include, but are not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The term "aggressive" or "invasive" with respect to cancer refers to the proclivity of a tumor for expanding beyond its boundaries into adjacent tissue (Darnell, J. (1990), Molecular Cell Biology, Third Ed., W. H. Freeman, NY). Invasive cancer can be contrasted with organ-confined cancer wherein the tumor is confined to a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

The term "metastasis", as used herein, refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

In a preferred embodiment, the urine sample is treated as to prevent degradation of Cyr61 protein. Methods for inhibiting or preventing degradation include, but are not limited to, treatment of the sample with protease, freezing the sample, or placing the sample on ice. Preferably, prior to analysis, the samples are constantly kept under conditions as to prevent degradation of Cyr61 protein.

As used herein, a "primary tumor" is a tumor appearing at a first site within the subject and can be distinguished from a "metastatic tumor" which appears in the body of the subject at a remote site from the primary tumor.

As used herein, "LCIS" refers to lobular carcinoma in situ. LCIS is also called lobular neoplasia and is sometimes classified as a type of noninvasive breast cancer. It does not penetrate through the wall of the lobules. Although it does not itself usually become an invasive cancer, women with this condition have a higher risk of developing an invasive breast cancer in the same or opposite breast.

As used herein, "DCIS" refers to ductal carcinoma in situ. Ductal carcinoma in situ is the most common type of noninvasive breast cancer. In DCIS, the malignant cells have not metastasized through the walls of the ducts into the fatty tissue of the breast. Comedocarcinoma is a type of DCIS that is more likely than other types of DCIS to come back in the same area after lumpectomy, and is more closely linked to eventual development of invasive ductal carcinoma than other forms of DCIS.

As used herein, "Cyr61" refers to the Cyr61 protein of Genebank accession, Genpept, O00622 and AAB58319 (Homosapiens) (SEQ ID NO:1) (FIG. 2). Cyr61 is a cysteine-rich, heparin-binding protein that is secreted and associated with the cell surface and extracellular matrix. The term "Cyr61" also encompasses species variants, homologues, allelic forms, mutant forms, and equivalents thereof.

The present invention is directed to methods for facilitating diagnosis of cancer of epithelial origin in a patient. In one embodiment, the method comprises measuring levels of Cyr61 in a test sample obtained from a subject, suspected of having cancer, and comparing the observed levels to levels of Cyr61 found in a control sample, for example a sample obtained from an individual patient or population of individuals that are believed not to have cancer. Levels of Cyr61 higher than levels that are observed in the normal control indicate the presence of cancer. The levels of Cyr61 can be represented by arbitrary units, for example as units obtained from a densitometer, luminometer, or an Elisa plate reader.

As used herein, "a higher level of Cyr61 in the test sample as compared to the level in the control sample" refers to an amount of Cyr61 that is greater than an amount of Cyr61 present in a control sample. The term "higher level" refers to a level that is statistically significant or significantly above levels found in the control sample. Preferably, the "higher level" is at least 2 fold greater.

The term "statistically significant" or "significantly" refers to statistical significance and generally means a two standard deviation (2 SD) above normal, or higher, concentration of the marker.

For purposes of comparison, the test sample and control sample are of the same type, that is, obtained from urine. However, the control sample can also be a standard sample that contains the same concentration of Cyr61 that is normally found in a urine sample obtained from a healthy individual.

In one aspect of the invention, a secondary diagnostic step can be performed. For example, if a level of Cyr61 is found to indicate the presence of cancer, then an additional method of detecting the cancer can be performed to confirm the presence of the cancer. Any of a variety of additional diagnostic steps can be used, such as mammography (breast cancer), ultrasound, PET scanning, MRI, or any other imaging techniques, biopsy, clinical examination, ductogram, or any other method.

Additionally, disease progression can be assessed by following Cyr61 levels in an individual patient. For example, changes in the patients condition can be monitored by comparing changes in Cyr61 expression levels in the patient over time. Progressive increases in Cyr61 levels is indicative of increased potential for tumor invasion and metastasis.

The prognostic methods of the invention also are useful for determining a proper course of treatment for a patient/subject having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

Measuring Levels of Cyr61

The levels of Cyr61 can be measured by any means known to those skilled in the art. In the present invention, it is generally preferred to use antibodies, or antibody equivalents, to detect Cyr61 levels. However, other methods for detection can also be used. For example, Cyr61 levels may be monitored by mass spectrometric analysis.

In one embodiment, levels of Cyr61 protein are measured by contacting the urine sample with an antibody-based binding moiety that specifically binds to Cyr61, or to a fragment of Cyr61. Formation of the antibody-Cyr61 complex is then detected as a measure of Cyr61 levels.

The term "antibody-based binding moiety" or "antibody" includes immunoglobulin molecules and immunologically active determinants of immunoglobulin molecules, e.g., molecules that contain an antigen binding site which specifically binds (immunoreacts with) to Cyr61, or to the additional biomarkers of the invention. The term "antibody-based binding moiety" is intended to include whole antibodies, e.g., of any isotype (IgG, IgA, IgM, IgE, etc), and includes fragments thereof which are also specifically reactive with Cyr61 protein. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dabs and single chain antibodies (scFv) containing a VL and VH domain joined by a peptide linker. The scFv's may be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the diagnostic and prognostic methods of the invention that use antibody based binding moieties for the detection of Cyr61 the level of Cyr61 protein present in the urine samples correlate to the intensity of the signal emitted from the detectably labeled antibody.

In one preferred embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished using any of a variety of other immunoassays. For example, by radioactively labeling an antibody, it is possible to detect the antibody though the use of radioimmune assays. The radioactive isotope can be detected by such means as the use of a gamma counter or a scintillation counter or by audoradiography. Isotopes which are particularly useful for the purpose of the present invention are $^3$H, $^{131}$I, $^{35}$S, $^{14}$C, and preferably $^{125}$I.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of Cyr61 can be detected by immunoassays, such as enzyme linked immunoabsorbant assay (ELISA), radioiimnunoassay (RIA), Immunoradiometric assay (IRMA), Western blotting, or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

"Radioimmunoassay" is a technique for detecting and measuring the concentration of an antigen using a labeled (e.g. radioactively labeled) form of the antigen. Examples of radioactive labels for antigens include $^3$H, $^{14}$C, and $^{125}$I. The concentration of antigen Cyr61 in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radiomimunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

A "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-Cyr61) is linked to a solid phase (i.e. a microtiter plate) and exposed to a biological sample containing antigen (e.g. Cyr61). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. Cyr61). The antigen-antibody mixture is then contacted with a solid phase (e.g. a microtiter plate) that is coated with antigen (i.e., Cyr61). The more antigen present in the sample, the less free antibody that will be available to bind to the solid phase. A labeled (e.g., enzyme linked) secondary antibody is then added to the solid phase to determine the amount of primary antibody bound to the solid phase.

In a "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or .beta.-galactosidase), or chemical methods (e.g., DAB/Substrate chromagen).

Other techniques may be used to detect the biomarkers of the invention, according to a practitioner's preference, and based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies that specifically bind to Cyr61 can then be used to assess Cyr61 levels, where the intensity of the signal from the detectable label corresponds to the amount of Cyr61 present. Levels can be quantitated, for example by densitometry.

Mass Spectometry

In addition, Cyr61 may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify proteins (see, e.g., Li et al. (2000) Tibtech 18:151-160; Rowley et al. (2000) Methods 20: 383-397; and Kuster and Mann (1998) Curr. Opin. Structural Biol. 8: 393-400), Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source.

The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio;.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one preferred embodiment, biomarker levels are measured by MALDI-TOF mass spectrometry.

Antibodies

The antibodies for use in the present invention can be obtained from a commercial source. Alternatively, antibodies can be raised against Cyr61, or a portion of the biomarker polypeptide.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702, 892 (U.S.A. Health & Human Services) and WO 01/18058 (Novopharm Biotech Inc.) disclose bacteriophage display libraries and selection methods for producing antibody binding domain fragments.

Cyr61 Detection Kit

The present invention is also directed to commercial kits for the detection and prognostic evaluation of a cancer of epithelial origin. The kit can be in any configuration well known to those of ordinary skill in the art and is useful for performing one or more of the methods described herein for the detection of Cyr61. The kits are convenient in that they supply many if not all of the essential reagents for conducting an assay for the detection of Cyr61 in a urine sample. In addition, the assay is preferably performed simultaneously with a standard or multiple standards that are included in the kit, such as a predetermined amount of Cyr61 protein, so that the results of the test can be quantitated or validated.

The kits include a means for detecting Cyr61 levels such as antibodies, or antibody fragments, which selectively bind to Cyr61 protein. The diagnostic assay kit is preferentially formulated in a standard two-antibody binding format in which one Cyr61 specific antibody captures Cyr61 in a patient sample and another Cyr61 specific antibody is used to detect captured Cyr61. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a calorimetric agent or radioisotope.

In one preferred embodiment, the kit comprises a means for detecting levels of Cyr61 in a sample of urine. In a specific embodiment, the kit comprises a "dipstick" with anti-Cyr61 antibodies or fragments, immobilized thereon, which specifically bind Cyr61 protein. Specifically bound Cyr61 protein can then be detected using, for example, a second antibody that is detectably labeled with a calorimetric agent or radioisotope.

In other embodiments, the assay kits may employ (but are not limited to) the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, and immunocytochemistry. For each kit the range, sensitivity, precision, reliability, specificity and reproducibility of the assay are established by means well known to those skilled in the art.

The above described assay kits would further provide instructions for use and a container designed for urine specimens.

All references cited above or below are herein incorporated by reference.

EXAMPLES

The present invention is further illustrated by the following Examples.

These Examples are provided to aid in the understanding of the invention and are not construed as a limitation thereof.

Example 1

Identification of Cyr61 as a Urinary Biomarker for Ovarian and Breast Cancer

Figure 1B:
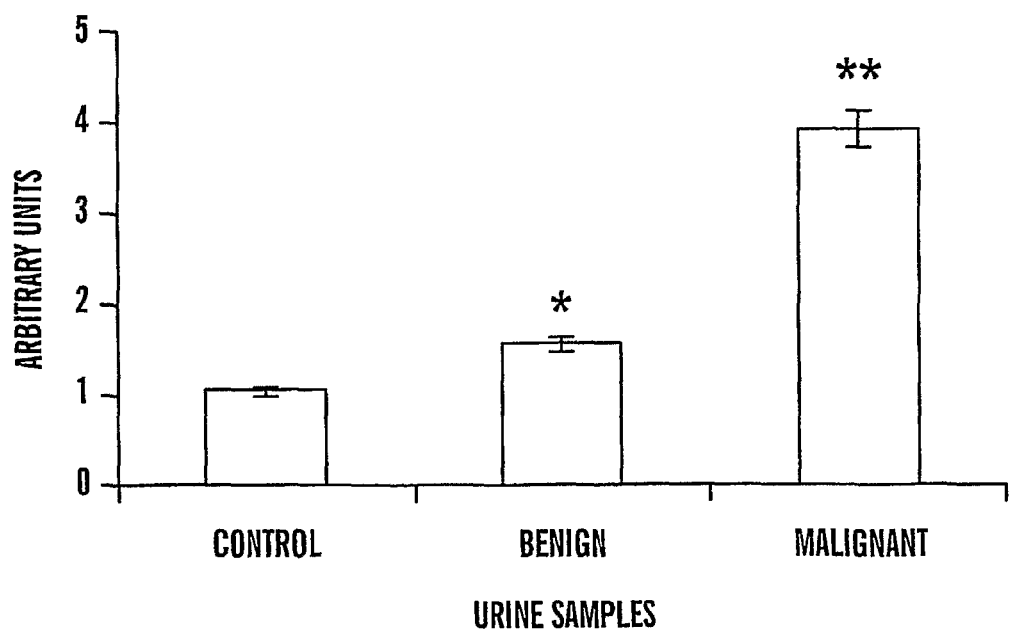

We have identified that Cyr61 protein serves a biomarker for ovarian cancer. In particular, we show that there is an increase in levels of Cyr61 in urine samples from patients that have benign and malignant ovarian cancer, as compared to control urine samples from patients that do not have cancer (FIGS. 1a and 1b). FIG. 1a shows immunoblot detection of ovarian cancer; Control lanes, control samples; Benign lanes, urine from a patients with benign cancer; lanes Malignant lanes, urine from a patients with malignant cancer. FIG. 1b shows a bar graph quantitation of the immunoblots detecting Cyr61 immunoreactive protein in urine from ovarian cancer patients (n=12 for each stage).

Figure 3:
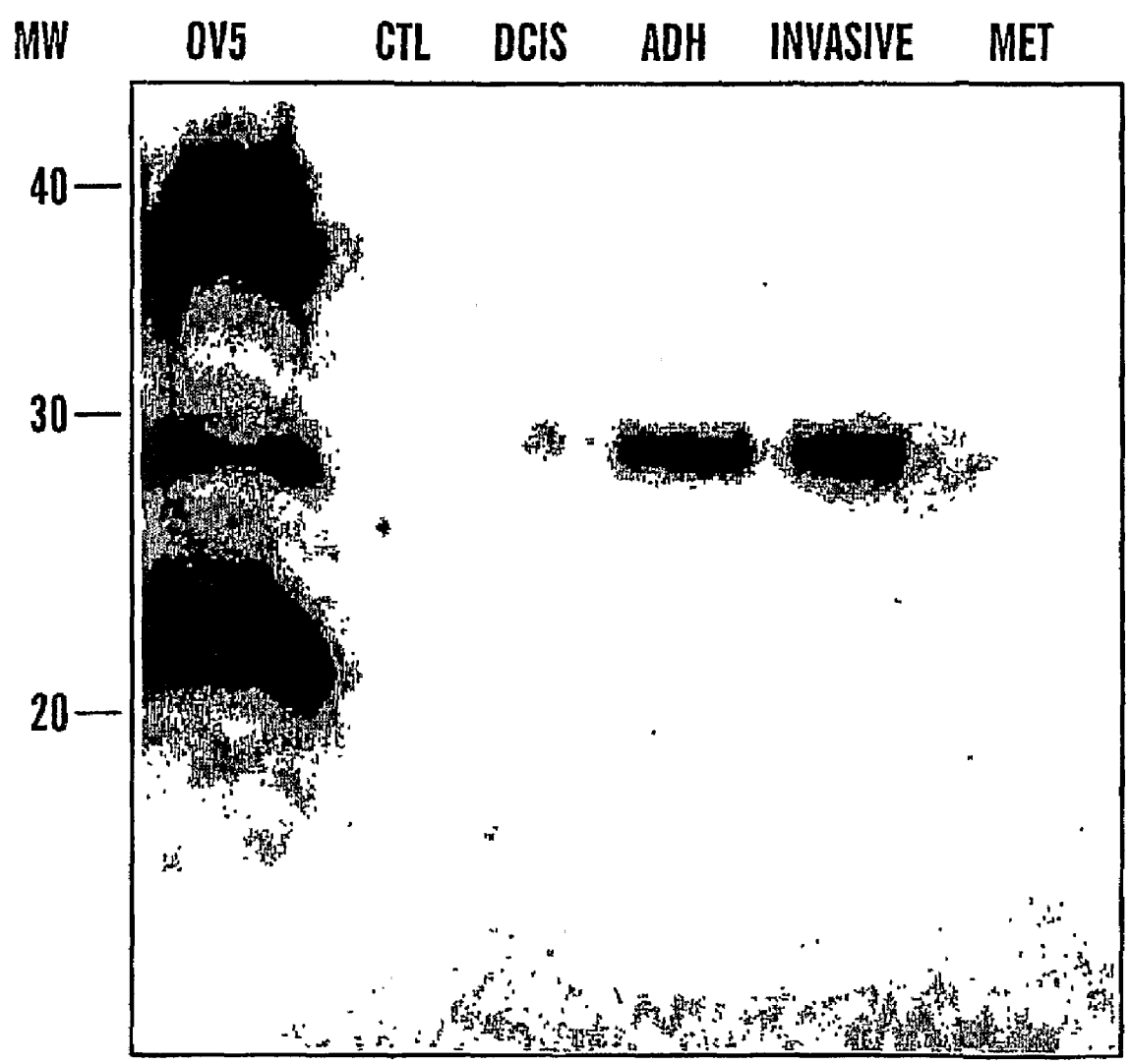
FIG. 3 shows a Western blot of CYR61 in urine from breast cancer patients. Cell lysate from ovarian cancer cell line OVCAR-5 (OV5) was used as positive control, lane 1. CYR61 immunoreactive protein was not detected in urine urine from age-, sex-matched healthy control (CTL) (lane 2), ductal carcinoma in situ (DCIS) (lane 3), atypical ductal hyperplasia (ADH) (lane 4), invasive (Invasive) (lane 6), and metastatic (Met) breast tumor patient (lane 7), respectively.

We also performed Western blotting of Cyr61 in urines from breast cancer patients (FIG. 3). There is an increase in levels of Cyr61 in urine samples from patients that have noninvasive (DCIS) and invasive breast cancer, as well as atypical ductal carcinoma (ADH), as compared to control urine samples from patients that do not have cancer.

Example 2

Cyr61 as a Regulator of the Angiogneic Switch

The formation and demise of the corpus luteum are accompanied with dramatic blood vessel formation and regression processes, respectively. This endocrine gland is therefore useful as a research model for elucidating the molecular mechanisms turning angiogenesis on and off. In the present study, we used PGF2α to induce regression of day 6 and day 10 corpus lutea. Luteal tissues were collected 30 minutes after PGF2α administration. Gene microarray analysis demonstrated Cyr61, an antiogenic inducer, was differentially expressed in both day 6 and 10 CL after PGF2α injection. Semi-quantitative RT-PCR further showed this gene was expressed at a significant higher (p<0.01) level in the early CL than the mid and late stages. In addition, Cyr61 expression was decreased during luteal regression. Immunohistochemistry revealed that Cyr61 protein was localized in both luteal endothelial and steroidogenic cells. To study the regulation of Cyr61, luteal steroidogenic and endothelial cells were isolated from mid-cycle CL and treated with PGF2α and TNFα. Although PGF2α had no effects on Cyr61 expression in both luteal steroidogenic and endothelial cells, TNFα stimulated Cyr61 expression in luteal endothelial cells, but decreased its transcriptional level in luteal steroidogenic cells. In conclusion, high expression of Cyr61 in the early CL suggests that this gene may be associated with luteal angiogenesis. The reduced level of Cyr61 in the regressing CL indicates the down-regulation of this gene may be a checkpoint for luteal regression. Moreover, TNFα differentially regulates Cyr61 expression in luteal endothelial and steroidogenic cells. Thus, the data suggests that Cyr61 is a key regulator of the angiogenesis switch, turning angiogenesis "on" and "off" during the life span of the corpus luteum.

Example III

Cyr61 As A Regulator Of In Epithelial Mesenchymal Transition (EMT)

To assess the potential role of Cyr61 in the development of aggressive cancer, we prepared stable OV5 (ovarian cell) cell lines that overexpress Cyr61 (OV5-Cyr61). We found that many molecules known to be involved in Epithelial Mesenchymal Transition (EMT) and migration/invasion are regulated by Cry61. Using RT-PCR and the cell lines that overexpress Cyr61, we found that upregulation of Cyr61 alters the expression of steroid receptors, integrin receptors, VEGF, and metalloprotienases (data not shown). For example, steroid receptor ERα expression is upregulated while AR expression is downregulated; MMP-9 expression (RT-PCR) and activity (via zymogram) are upregulated, as well as MMP-1, MMP-8, MMP-3, MMP-23, MMP-19 expression, while there appears to be no effect on MMP-13, MMP-10 and MT1-MMP expression; MMP-7 expression is downregulated; β6, β3, α6 and αV integrin expression are upregulated; and VEGF-A and VEGF-C are upregulated in these cell lines.

Using the OV5-Cyr61 cell lines, we further determined, by ELISA assay, that Cyr61 stimultes VEGF-A protein levels (data not shown). Using RT-PCR we also found that the EMT-related transcription factor Snail is upreglated, while SIP-1, Twist, and Slug appear to be unaffected.

In further support of the involvement of Cyr61 in development of aggressive cancer, we performed scratch migration and tumor invasion assays. A modified scratch migration assay was employed to assess cell motility. Briefly, vector control and CYR61-overexpressing OVCAR-5 cells were cultured in 60 mm Petri dish. After cells were confluent, a scratch (no cell zone) was made by a sterile pipette tip. The floating cells were cleared away by washing three times with medium. Cells were incubated with fresh medium for 5 hours. The distances between the two edges of the scratch were recorded before and after incubation. Cell motility rate was calculated by reduction of the distance divided by incubation time. The results of this assay clearly show that overexpression of Cyr61 increases motility. Cells overexpressing Cyr61 migrated twice as far than cells that did not overexpress Cyr61 (data not shown).

The invasiveness of CYR61 overexpressing cells was evaluated using a 24-well tumor invasion system (BD Bioscience, Bedford, Mass.) according to manufacture's manual. OVCAR-5 vector control and CYR61-overexpressing cells were grown to 70% confluence and were then trypsinized and resuspended in serum-free medium. $5 \times 10^4$ cells were seeded into the top chambers. Full media (750 μl) were used as chemoattractant and were added into the lower chambers. After incubation in 37° C., 5% $CO_2$ incubator for 24 hours, medium was removed from upper chambers. The insert plates were then transferred to a new 24 well plate containing 0.5 ml/well of 4 μg/ml Calcein AM in Hanks Buffered Salt Solution (HBSS) and were incubated for 1 hour at 37° C., 5% $CO_2$. The BD FluoroBlok membrane only allows the labeled cells that invaded through BD Matrigel™ Membrane to be visualized under fluorescence microscope. The results of this assay show that overexpression of Cyr61 increases invasiveness (data not shown).

Thus, Cyr61 is involved in the development of cell phenotypes consistent with what is found in aggressive cancers

REFERENCES

The references cited here and throughout the specification are hereby incorporated by reference.
1. Evtimova V, Zeillinger R, Weidle U H. Identification of genes associated with the invasive status of human mammary carcinoma cell lines by transcriptional profiling Tumour Biol. 2003 August-September; 24(4):189-98.
2. Planque N, Perbal B. A structural approach to the role of CCN (CYR61/CTGF/NOV) proteins in tumourigenesis. Cancer Cell Int. 2003 August 22; 3(1):15.
3. Menendez J A, Mehmi I, Griggs D W, Lupu R The angiogenic factor CYR61 in breast cancer: molecular pathology and therapeutic perspectives. Endocr Relat Cancer. 2003 June; 10(2):141-52. Review.
4. Tsai M S, Bogart D F, Castaneda J M, Li P, Lupu R. Cyr61 promotes breast tumorigenesis and cancer progression. Oncogene. 2002 November 21; 21(53):8178-85.
5. Tsai M S, Bogart D F, Li P, Mehmi I, Lupu R. Expression and regulation of Cyr61 in human breast cancer cell lines. Oncogene, 2002 January 31; 21(6):964-73.
6. Tsai M S and Ruth Lupu. An angiogenic factor, in breast cancer tumor progression. International Journal of Molecular Medicine, 2000, 6: S22 Abstract.
7. Xie D, Miller C W, O Kelly J, Nakachi K, Sakashita A, Said J W, Gombein J, Koeffler H P. Breast cancer. Cyr61 is overexpressed, estrogen-inducible, and associated with more advanced disease.
8. J Biol Chem. 2001 April 27; 276(17):14187-94. pub 2001 January 31.
9. Xie D, Nakachi K, Sakashita A., Higashi, Miller C W, and Phillip Koeffler. CYR61, an angiogenic induce, is overexpressed and estrogen inducible in breast cancer. Proc. Amer. Assoc. for Cancer Research, 2000, 41: 338. Abstract.
10. Tsai et al. Cyr61 induces breast tumorigenicity and promotes breast cancer progression through regulation of the MAPK and AKT signaling pathways. Proc. Amer. Assoc. for Cancer Research, 2002, 43: 673. Abstract.
11. Perbal et al. Report on the second international workshop on the CCN family of genes. J. Clin. Pathol: Mol Pathol. 2003, 56: 80-85.
12. Cayer-Lelievre et al. Report on the first international workshop on the CCN family of genes J. Clin. Pathol: Mol Pathol. 2001, 54: 105-107.

We claim:

1. A method for facilitating the diagnosis of a subject for breast cancer comprising:
   a. measuring Cyr61 levels present in a test urine sample obtained from the subject;
   b. comparing the level of Cyr61 in the test urine sample with the level of Cyr61 present in a control urine sample;
   wherein a higher level of Cyr61 in the test sample as compared to the level of Cyr61 in the control sample is indicative of breast cancer.

2. The method of 1, wherein the level of Cyr61 protein is measured by a method comprising the steps of:
   a. contacting the test sample, or preparation thereof, with an antibody-based binding moiety which specifically binds Cyr61 to form an antibody-Cyr61 complex; and
   b. detecting the presence of the complex, thereby measuring the level of Cyr61 present.

3. The method according to claim 2, wherein the antibody-based binding moiety is labeled with a detectable label.

4. The method according to claim 3, wherein the label is selected from the group consisting of a radioactive label, a hapten label, a fluorescent label, and an enzymatic label.

5. The method according to claim 2, wherein the antibody-based binding moiety is an antibody.

6. The method according to claim 5, wherein the antibody is an monoclonal antibody.

7. A method to direct treatment of a subject which comprises having a subject tested for the levels of Cyr61 in a urine sample obtained from the subject, wherein a clinician reviews the results and if the subject's urine sample has a higher level of Cyr61 than the level of Cyr61 in the control sample, the clinician directs the subject to be treated for breast cancer.

8. The method of claim 1, wherein the level of Cyr61 in the test sample is at least 1.5-fold higher than in the control sample.

9. The method of claim 1, wherein the level of Cyr61 in the test sample is at least 2-fold higher than in the control sample.

10. The method of claim 1, wherein the level of Cyr61 protein is measured by mass spectrometric analysis.

11. The method of claim 1, wherein the level of Cyr61 protein is measured by an antibody.

12. The method of claim 1, wherein the level of Cyr61 protein is measured by enzyme linked immunoabsorbant assay (ELISA).

13. The method of claim 1, wherein the level of Cyr61 protein is measured by radioimmunoassay (RIA).

14. The method of claim 1, wherein the level of Cyr61 protein is measured by immunoradiometric assay (IRMA).

15. The method of claim 1, wherein the level of Cyr61 protein is measured by Western blotting.

16. The method of claim 1, wherein the level of Cyr61 protein is measured by a protein chip.

* * * * *

UNITED STATES PATENT AND TRADEMARK OFFICE
CERTIFICATE OF CORRECTION

PATENT NO. : 7,858,324 B2  
APPLICATION NO. : 11/815831  
DATED : December 28, 2010  
INVENTOR(S) : Marsha A. Moses et al.

Page 1 of 1

It is certified that error appears in the above-identified patent and that said Letters Patent is hereby corrected as shown below:

Claim 2, column 17, line 21, insert --claim-- after the "The method of"

Signed and Sealed this
Fifteenth Day of February, 2011

David J. Kappos
*Director of the United States Patent and Trademark Office*